United States Patent [19]

Ernst

[11] Patent Number: 5,218,097
[45] Date of Patent: Jun. 8, 1993

[54] PROCESS FOR THE PREPARATION OF PROTECTED MONO-SUGAR AND OLIGO-SUGAR HALIDES

[75] Inventor: Beat Ernst, Magden, Switzerland

[73] Assignee: Ciba-Geigy Corporation, Ardsley, N.Y.

[21] Appl. No.: 442,102

[22] Filed: Nov. 28, 1989

[30] Foreign Application Priority Data

Dec. 7, 1988 [CH] Switzerland .................. 4529/88

[51] Int. Cl.$^5$ .............................................. C07H 1/00
[52] U.S. Cl. .................................. 536/18.5; 536/17.2; 536/18.4; 536/18.7; 536/115; 536/122; 536/124
[58] Field of Search .................. 536/18.4, 122, 18.7, 536/17.2, 18.5, 124, 115

[56] References Cited

U.S. PATENT DOCUMENTS

| 4,321,366 | 3/1982 | Bobek et al. | 536/122 |
| 4,324,888 | 4/1982 | Rathbone | 536/122 |
| 4,751,291 | 6/1988 | Thiem et al. | 536/18.4 |
| 4,783,526 | 11/1988 | O'Brien et al. | 536/18.4 |
| 4,977,254 | 12/1990 | Homer et al. | 536/18.4 |

FOREIGN PATENT DOCUMENTS 2045246 10/1980 United Kingdom .
2221462 7/1990 United Kingdom .

OTHER PUBLICATIONS

Tetrahedron letters, vol. 26, #1, p. 3.
Tetrahedron letters, vol. 21, pp. 1421–1424.
Helvetica Chimica Acta–vol. 68 (1985) pp. 283–287.
Carbohydrate Research 34 (1974) 71–78.
Carbohydrate Research 24 (Jan. 31, 1972) pp. 45–56.
Beat Ernst et al., Helvetica Chimica Acta –vol. 72 (1989).
Synthesis–Journal of Synthetic Organic Chemistry–pp. 361–366; Ulrich Schmidt et al., May 1986.
Marc Van Robays et al., Journal of the Chemical Society-Perkin Transactions 1, pp. 251–254 (1986).
Journal of Chemical Society Chemical Communications, No. 24, p. 1113, Alan T. Hutton et al. (1979).
Alain Devos et al., J.C.S. Chem. Comm. pp. 1180–1181 (1979).
Beat Ernst et al., Tetrahedron Letters, vol. 30, No. 23, pp. 3081–3084 (1989)–Printed in Great Britain.

Primary Examiner—Johnnie R. Brown
Assistant Examiner—Everett White
Attorney, Agent, or Firm—Kevin T. Mansfield

[57] ABSTRACT

The reaction of protected monosaccharides or oligosaccharides or protected monosaccharide and oligosaccharide derivatives containing an anomeric hydroxyl group with secondary α-haloenamines affords high yields of protected glycosyl halides, which are valuable intermediates for the introduction of sugar groups in the synthesis of oligosaccharides, glycolipids or glycopeptides.

17 Claims, No Drawings

PROCESS FOR THE PREPARATION OF PROTECTED MONO-SUGAR AND OLIGO-SUGAR HALIDES

The invention relates to a process for the preparation of protected mono-sugar and oligo-sugar halides or halogenated mono-sugar or oligo-sugar derivatives having anomeric halogen atoms (glycosyl halides) in which a protected sugar, or an appropriate sugar derivative, containing an anomeric hydroxyl group is reacted with a secondary α-haloenamine.

Protected glycosyl halides are important intermediates for the introduction of sugar groups. Various processes using a variety of halogenating agents are known for the preparation of glycosyl halides.

In Helv. Chim. Acta, Volume 68, pages 283-287 (1985), H. Kunz et al. describe the preparation of glycosyl fluorides using HF or triphenylphosphine/diethyl azodicarboxylate/triethyloxonium tetrafluoborate. In Tetrahedron Letters, Volume 26, pages 3-4 (1985), W. Rosenbrook et al. suggest wet diethylaminosulfur trifluoride as a fluorinating agent for the preparation of glycosyl fluorides.

In Carbohydr. Res., Volume 24, pages 45-56 (1972), S. Hanessian et al. describe the halogenation of the anomeric hydroxyl group of sugars by means of triphenylphosphine/N-chloro-, N-bromo- or N-iodo-succinimide.

In Tetrahedron Letters, Volume 21, pages 1421-1423 (1980), R. Schmidt et al. describe the chlorination of the anomeric hydroxyl group of a sugar acid ester using thionyl chloride, and its bromination using $PBr_3$.

In Carbohyd. Res., Volume 34, pages 71-78 (1974), F.J. Kronzer et al. describe the in situ-preparation of anomeric glycosyl iodides by reacting glycosyl chlorides with NaI.

The invention relates to a process for the preparation of protected sugar halides or halogenated sugar derivatives having an anomeric halogen atom by halogenating the anomeric hydroxyl group, which process comprises reacting 1 equivalent of a protected sugar or a protected sugar derivative containing an anomeric hydroxyl group with at least one equivalent of a secondary α-haloenamine in an inert solvent.

The process is preferably carried out at a temperature from $-20°$ to $80°$ C., particularly $0°$ to $60°$ C.

The solvent preferably used is a halogenated aliphatic hydrocarbon, an aromatic hydrocarbon or an aliphatic ether. Examples of inert solvents are $CH_2Cl_2$, $CHCl_3$, $CCl_4$, 1,2-dichloroethane, 1,1,2,2-tetrachloroethane, benzene, toluene, xylene, diethyl ether, dibutyl ether, ethylene glycol dimethyl ether, tetrahydrofuran and dioxane.

The α-haloenamine is preferably used in an amount of 1 to 3, particularly 1.5 to 2.5, equivalents per equivalent of protected sugar.

The process is advantageously carried out under an atmosphere of a protective gas, for example under an atmosphere of $N_2$ or a noble gas.

A preferred embodiment of the process is one wherein the α-haloenamine has the formula I

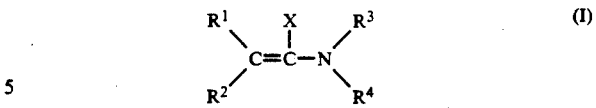

in which $R^1$ and $R^2$ independently of one another are linear or branched $C_1$–$C_{12}$alkyl, $C_4$–$C_7$cycloalkyl, $C_1$–$C_{12}$alkyl-$C_4$–$C_7$cycloalkyl, $C_4$–$C_7$cycloalkylmethyl, $C_1$–$C_{12}$alkyl-$C_4$–$C_7$cycloalkylmethyl, phenyl, $C_1$–$C_{12}$alkylphenyl, benzyl or $C_1$–$C_{12}$alkylbenzyl, or $R^1$ and $R^2$ together are tetramethylene, pentamethylene or hexamethylene; $R^3$ and $R^4$ independently of one another are linear or branched $C_1$–$C_{12}$alkyl, $C_4$–$C_7$cycloalkyl, $C_1$–$C_{12}$alkyl-$C_4$–$C_7$cycloalkyl, $C_4$–$C_7$cyclalkylmethyl, $C_1$–$C_{12}$alkyl-$C_4$–$C_7$cycloalkylmethyl, phenyl or benzyl, or $R^3$ and $R^4$ together are tetramethylene, pentamethylene or 3-oxa,-1,5-pentylene; and X is halogen.

Examples of $R^1$, $R^2$, $R^3$ and $R^4$ as alkyl can be methyl, ethyl and the isomers of propyl, butyl, pentyl, hexyl, heptyl, octyl, nonyl, decyl, undecyl and dodecyl.

Examples of $R^1$, $R^2$, $R^3$ and $R^4$ as cycloalkyl can be cyclobutyl, cyclopentyl, cyclohexyl and cycloheptyl. Cyclopentyl and cyclohexyl are preferred.

$R^1$, $R^2$, $R^3$ and $R^4$ as alkylcycloalkyl are preferably $C_1$–$C_6$alkylcyclopentyl and especially $C_1$–$C_6$alkylcyclohexyl. Some examples are methylcyclobutyl, methylcyclopentyl, ethylcyclopentyl, methylcyclohexyl, ethylcyclohexyl, n-, iso- or t-butylcyclohexyl, dimethylcyclohexyl or methylethylcyclohexyl.

Examples of $R^1$, $R^2$, $R^3$ and $R^4$ as cycloalkylmethyl can be cyclopentylmethyl and cyclohexylmethyl.

Examples of $R^1$, $R^2$, $R^3$ and $R^4$ as alkylcycloalkylmethyl can be $C_1$–$C_6$alkylcyclopentylmethyl or $C_1$–$C_6$alkylcyclohexylmethyl. Examples are (methylcyclopentyl)-methyl, (methylcyclohexyl)-methyl, (butylcyclohexyl)-methyl and (dimethylcyclohexyl)-methyl.

$R^1$ and $R^2$ as alkylphenyl are preferably $C_1$–$C_6$alkylphenyl, and as alkylbenzyl are preferably $C_1$–$C_6$alkylbenzyl. Examples are methylphenyl, dimethylphenyl, ethylphenyl, n-propylphenyl, isopropylphenyl, n-, iso- or t-butylphenyl, methylbenzyl, dimethylbenzyl, ethylbenzyl, n-propylbenzyl, isopropylbenzyl or n-, iso- or t-butylbenzy.

As halogen, X is —F, —Cl, —Br or —I.

Preferably, $R^1$ and $R^2$ and also $R^3$ and $R^4$ independently of one another are $C_1$–$C_6$alkyl. Particularly preferably, $R^1$ and $R^2$ are each methyl. $R^3$ and $R^4$ are especially $C_1$–$C_4$alkyl. In particular, $R^3$ and $R^4$ are identical and are methyl, ethyl, n-propyl or isopropyl.

The preparation of secondary α-chloroenamines is described in Organic Synthesis 59, pages 26-34 (1979). Of these, α-fluoro-, α-bromo- and α-iodo-enamines can be prepared by the process described by L. Ghosez et al. in J. Chem. Soc. Chem. Comm., page 1180 (1979).

The protected sugars used in the process according to the invention are known and can be prepared by known processes and many of the sugars are commercially available. They can, for example, be protected monosaccharides and oligosaccharides, for examples mono-, di-, tri-, tetra- and penta-saccharides. In a preferred embodiment, the protected monosaccharides and oligosaccharides are an aldose or ketose having an anomeric hydroxyl group. In a particularly preferred embodiment, the protected monosaccharide is selected from aldopyranoses, aldohexoses, aldofuranoses, ketopyranoses or ketofuranoses having an anomeric hydroxyl group. The aldopyranose is especially D-ribose, D-arabinose, D-xylose or D-lyxose; the aldohexose is D-allose, D-altrose, D-glucose, D-mannose, D-gulose, D-idose, D-galactose or D-talose and the ketofuranose is D-psicose, D-fructose, D-sorbose or D-tagtose, the hydroxyl groups thereof apart from the anomeric hydroxyl group, being protected.

In particular, the disaccharide is trehalose, sophorose, kojibiose, laminaribiose, maltose, cellobiose, isomaltose, gentobiose, sucrose, raffinose and lactose, the hydroxyl groups thereof, apart from the anomeric hydroxyl group, being protected.

Protected monosaccharide and oligosaccharide derivatives having an anomeric hydroxyl group are known, can be prepared by known processes and, in part, are commercially available. Possible examples are protected deoxy-sugars, amino-sugars, thio-sugars, sugar acids or esters of sugar acids containing an anomeric hydroxyl group, for example 2-deoxy-sugars, 2-thio-sugars, 2-amino-sugars and gluconic acids and esters thereof, preferably their $C_1$-$C_4$alkyl esters.

Protected means that the hydroxyl groups of the monosaccharides and oligosaccharides or monosaccharide and oligosaccharide derivatives other than the anomeric hydroxyl group are derivatised by a detachable protective group. Protective groups of this type and processes for forming derivatives are generally known in sugar chemistry. The following are examples of protective groups of this type: linear or branched $C_1$-$C_8$alkyl, especially $C_1$-$C_4$alkyl, for example methyl, ethyl, n-propyl, isopropyl or n-, iso- and t-butyl; $C_7$-$C_{12}$aralkyl, for example benzyl, trialkylsilyl having 3 to 20, particularly 3 to 10, C atoms, for example trimethylsilyl, triethylsilyl, tri-n-propylsilyl, isopropyldimethylsilyl, t-butyldimethylsilyl, n-octyldimethylsily or (1,1,2,2-tetramethylethyl)-dimethylsily; substituted methylidene groups which are obtainable by forming acetals or ketals from adjacent OH groups of the sugars or sugar derivatives by means of aldehydes and ketones and which preferably contain 2 to 12, or 3 to 12, respectively, C atoms, for example $C_1$-$C_{12}$alkylidene, preferably $C_1$-$C_6$alkylidene and particularly $C_1$-$C_4$alkylidene, or benzylidene (ethylidene, 1,1-propylidene, 2,2-propylidene, 1,1-butylidene or 2,2-butylidene); $C_2$-$C_{12}$acyl, especially $C_2$-$C_8$acyl, for example aetyl, propanoyl, butanoyl, pentanoyl, hexanoyl and benzoyl; $R^5$—$SO_2$—, in which $R^5$ is $C_1$-$C_{12}$alkyl, especially $C_1$-$C_6$alkyl, $C_5$cycloalkyl, $C_6$cycloalkyl, phenyl, benzyl or $C_1$-$C_{12}$alkylphenyl, especially $C_1$-$C_4$alkylphenyl, or $C_1$-$C_{12}$alkylbenzyl, especially $C_1$-$C_4$alkylbenzyl, for example methylsulfonyl, ethylsulfonyl, propylsulfonyl, butylsulfonyl, phenylsulfonyl, benzylsulfonyl and p-methylphenylsulfonyl.

The process according to the invention can, for example, be carried out in such a way that 1 equivalent of a protected monosaccharide or oligosaccharide or monosaccharide or oligosaccharide derivative is dissolved in a solvent, and at least 1 equivalent of secondary α-haloenamine is added, preferably under a protective gas atmosphere (nitrogen or argon), it being advantageous to maintain the temperature at −20° to +20° C., especially about 0° C. The reaction is then allowed to proceed to complete conversion, advantageously at an elevated temperature of, for example, up to 80° C.

The glycosyl halides can be isolated, for example, by first concentrating the reaction mixture by distillation, if appropriate in vacuo. The residue can either be employed without further treatment for glycolization reactions or can be purified further by means of customary methods (distillation, crystallization or chromatographic methods).

Surprisingly, the process according to the invention makes it possible to prepare any glycosyl halide by means of only one halogenating agent, high yields and selectivities being achieved at the same time. The reaction proceeds under entirely neutral conditions, so that it is also possible to use sugars having acid-labile and base-labile protective groups or else sugar derivatives containing labile groups of this type, for example silyl ether groups. It is also possible, by means of the process according to the invention, to avoid the autocatalytic decomposition of the bromoglycosides and iodoglycosides which is observed in other processes of preparation.

The glycosyl halides are suitable for the introduction of sugar groups in the synthesis of oligosaccharides, glycolipids or glycopeptides, see, for example, H. Paulsen, Chem. Soc. Rev., 13, pages 15–45 (1984) and R. R. Schmidt, Angew. Chem. 98, 213–236 (1986).

The following examples illustrate the invention in greater detail.

EXAMPLE 1

229 µl (1.62 mmol) of 1-chloro-N,N-2-trimethyl-propenylamine are added to 513 mg (1.47 mmol) of 2,3,4,6-tetra-O-acetylmannopyranose in 5 ml of anhydrous chloroform at 0° C. under argon. The mixture is then stirred for 20 hours at room temperature. The reaction mixture is concentrated and chromatographed over silica gel 60 using 2:1 40°–60° petroleum ether-/ethyl acetate. This gives 406 mg (75%) of 2,3,4,6-tetra-O-acetyl-α-D-mannopyranosyl chloride.

$^1$H-NMR (300 MHz, CDCl$_3$): 5.99 (d, J=1.7, H-C(1)).

EXAMPLE 2

514 mg (84%) of 2,3,4,6-tetra-O-acetyl-α-D-mannopyranosyl bromide are obtained analogously to Example 1, starting from 521 mg (1.49 mmol) of 2,3,4,6-tetra-O-acetyl-mannopyranose and 234 µl (1.64 mmol) of 1-bromo-N,N-2-trimethylpropenylamine.

$^1$H-NMR (300 MHz, CDCl$_3$): 6.30 (d, J=1.6, H-C(1)).

EXAMPLE 3

545 mg (79%) of 2,3,4,6-tetra-O-acetyl-α-D-mannopyranosyl iodide are obtained analogously to Example 1, starting from 527 mg (1.51 mmol) of 2,3,4,6-tetra-O-acetyl-mannopyranose and 272 µl (1.66 mmol) of 1-iodo-N,N-2-trimethylpropenylamine.

$^1$H-NMR (300 MHz, CDCl$_3$): 6.71 (d, J=1.6, H-C(1)).

EXAMPLE 4

450 mg (98% α:β=6:1) of 2,3,4,6-tetra-O-acetyl-α-D-mannopyranosyl fluoride are obtained analogously to Example 1, starting from 455 mg (1.30 mmol) of 2,3,4,6-tetra-O-acetyl-mannopyranose and 289 µl (1.43 mmol) of 1-fluoro-N,N-diisopropyl-2-methylpropenylamine.

$^1$H-NMR (300 MHz, CDCl$_3$): 5.58 (dd, $J_{1,f}$=48.5, $J_{1,2}$=1.9, β-H-C(1)); 5.55 (dd, $J_{1,F}$=49.5, $J_{1,2}$=1.7, α-H-C(1)).

EXAMPLE 5

964 mg (91%) of 2,3,4,5-tetra-O-acetyl-α-D-glucopyranosyl chloride are obtained analogously to Example 1, starting from 1.00 g (2.87 mmol) of 2,3,4,6-tetra-O-acetyl-glucopyranose and 0.81 ml (5.74 mmol) of 1-chloro-N,N-2-trimethylpropenylamine.

$^1$H-NMR (300 MHz, CDCl$_3$): 6.30 (d, J=3.9, H-C(1)).

EXAMPLE 6

450 mg (77%) of 2,3,4,6-tetra-O-acetyl-α-D-glucopyranosyl bromide are obtained analogously to Example 1, starting from 494 mg (1.41 mmol) of 2,3,4,6-tetra-O-acetyl-glucopyranose and 201 µl (1.41 mmol) of 1-bromo-N,N-2-trimethylpropenylamine.

$^1$H-NMR (300 MHz, CDCl$_3$): 6.61 (d, J=4, H-C(1)).

EXAMPLE 7

556 mg (84%) of 2,3,4,6-tetra-O-acetyl-α-D-glucopyranosyl iodide are obtained analogously to Example 1, starting from 506 mg (1.45 mmol) of 2,3,4,6-tetra-O-acetyl-glucopyranose and 475 µl (2.90 mmol) of 1-iodo-N,N-2-trimethylpropenylamine.

$^1$H-NMR (300 MHz, CDCl$_3$): 6.99 (d, J=4, H-C(1)).

EXAMPLE 8

386 mg (85%, α:β=1:3) of 2,3,4,6-tetra-O-acetyl-α-D-glucopyranosyl fluoride are obtained analogously to Example 1, starting from 455 mg (1.30 mmol) of 2,3,4,6-tetra-O-acetyl-glucopyranose and 527 µl (2.61 mmol) of 1-fluoro-N,N-diisopropyl-2-methylpropenylamine.

$^1$H-NMR (300 MHz, CDCl$_3$): 5.75 (dd, $J_{1,F}$=53, $J_{1,2}$=3, β-H-C(1)); 5.37 (dd, $J_{1,F}$=52, $J_{1,2}$=6, α-H-C(1)).

EXAMPLE 9

517 mg (92%) of 2,3,4,6-tetra-O-benzyl-α-D-glucopyranosyl chloride are obtained analogously to Example 1, starting from 540 mg (1.0 mmol) of 2,3,4,6-tetra-O-benzyl-D-glucopyranose and 156 µl (1.1 mmol) of 1-chloro-N,N-2-trimethylpropenylamine.

$^1$H-NMR (300 MHz, CDCl$_3$): 6.06 (d, J=3.7, H-C(1)).

EXAMPLE 10

224 mg (98%) of 2,3,4,6-tetra-O-benzyl-α-D-glucopyranosyl bromide are obtained analogously to Example 1, starting from 203 mg (0.37 mmol) of 2,3,4,6-tetra-O-benzyl-D-glucopyranose and 80 µl (0.56 mmol) of 1-bromo-N,N-2-trimethylpropenylamine.

$^1$H-NMR (300 MHz, CDCl$_3$): 6.43 (d, J=3.7, H-C(1)).

EXAMPLE 11

498 mg (99%; α:β=28:72) of 2,3,4,6-tetra-O-benzyl-α-D-glucopyranosyl fluoride are obtained analogously to Example 1, starting from 500 mg (0.925 mmol) of 2,3,4,6-tetra-O-benzyl-D-glucopyranose and 373 µl (1.85 mmol) of 1-fluoro-N-N-diisopropyl-2-methylpropenylamine.

$^1$H-NMR (300 MHz, CDCl$_3$): 5.55 (dd, $J_{1,F}$=53, $J_{1,2}$=2.8, β-H-C(1)); 5.25 (dd, $J_{1,F}$=52.7, $J_{1,2}$=6.5, α-H-C(1)).

EXAMPLE 12

2,3,4,6-Tetra-O-benzyl-α-D-glucopyranosyl iodide is obtained quantitatively analogously to Example 1, starting from 381 mg (0.70 mmol) of 2,3,5,6-tetra-O-benzyl-D-glucopyranose and 346 µl (2.11 mmol) of 1-iodo, N,N-2-trimethylpropenylamine, after the reaction mixture has been concentrated.

$^1$H-NMR (300 MHz, CDCl$_3$): 6.85 (d, J=4, H-C(1)).

EXAMPLE 13

40 mg (20%) of 2,3:5,6-bis-O-(1-methylethylidene)-α-D-mannofuranosyl fluoride and 114 mg (57%) of 2,3:5,6-bis-O-(methylethylidene)-β-D-mannofuranosyl fluoride are obtained analogously to Example 1, starting from 198 mg (0.76 mmol) of 2,3:5,6-bis-O-(1-methylethylidene)-α-D-mannofuranose and 306 µl (1.52 mmol) of 1-fluoro-N,N-diisopropyl-2-methylpropenylamine.

$^1$H-NMR (300 MHz, CDCl$_3$): 5.69 (d, $J_{1,F}$=59.3, β-H-C(1)); 5.51 (dd, $J_{1,F}$=66.6, $J_{1,2}$=3.7, α-H-C(1)).

EXAMPLE 14

170 mg (78%) of 2,3:5,6-bis-O-(1-methylethylidene)-α-D-mannofuranosyl chloride are obtained analogously to Example 1, starting from 203 mg (0.77 mmol) of 2,3:5,6-bis-O-(1-methylethylidene)-α-D-mannofuranose and 122 µl (0.85 mmol) of 1-chloro-N,N-2-trimethylpropenylamine.

$^1$H-NMR (300 MHz, CDCl$_3$): 6.08 (s, α-H-C(1)).

EXAMPLE 15

220 mg (90%) of 2,3:5,6-bis-O-(1-methylethylidene)-α-D-amnnofuranosyl bromide are obtained analogously to Example 1, starting from 199 mg of 2,3:5,6-bis-O-(1-methylethylidene)-α-D-mannofuranose and 239 µl (1.69 mmol) of 1-bromo-N,N-2-trimethylpropenylamine, after the reaction mixture has been concentrated.

$^1$H-NMR (300 MHz, CDCl$_3$): 6.39 (S, α-H-C(1)).

EXAMPLE 16

192 mg (72%) of 2,3:5,6-bis-O-(1-methylethylidene)-α-D-mannofuranosyl iodide are obtained analogously to Example 1, starting from 187 mg (0.71 mmol) of 2,3:5,6-bis-O-(1-methylethylidene)-α-D-mannofuranose and 235 µl (1.43 mmol) of 1-iodo, N,N-2-trimethylpropenylamine after the reaction mixture has been concentrated.

$^1$H-NMR (300 MHz, CDCl$_3$): 6.63 (d, J=1, β-H-C(1)).

EXAMPLE 17

161 (76%) of methyl 2,3,4-tri-O-acetyl-1-deoxy-1-fluoro-D-glucuronate (β:α=9:1) are obtained analogously to Example 1, starting from 210 mg (0.62 mmol) of methyl 2,3,4-tri-O-acetyl-D-glucuronate and 253 µl (1.25 mmol) of 1-fluoro-N,N-diisopropyl-2-methylpropenylamine.

$^1$H-NMR (300 MHz, CDCl$_3$): 5.82 (dd, $J_{1,F}$=53, $J_{1,2}$=3, β-H-C(1)); 5.45 (dd, $J_{1,F}$=51, $J_{1,2}$=5, α-H-C(1)).

EXAMPLE 18

169 mg (88%) of methyl 2,3,4-tri-O-acetyl-1-deoxy-1chloro-D-glucuronate (α:β=18:82) are obtained analogously to Example 1, starting from 191 mg (0.57 mmol) of methyl 2,3,4-tri-O-acetyl-D-glucuronate and 89 µl (0.62 mmol) of 1-chloro-N,N-2-trimethylpropenylamine.

$^1$H-NMR (300 MHz, CDCl$_3$): 6.34 (d, J=4, β-H-C(1)); 5.36 (d, J=8, α-H-C(1)).

EXAMPLE 19

Methyl 2,3,4-tri-O-acetyl-1-deoxy-1-bromo-α-D-glucuronate is obtained quantitatively analogously to Example 1, starting from 199 mg (0.59 mmol) of methyl 2,3,4-tri-O-acetyl-D-glucuronate and 186 µl (1.30 mmol) of 1-bromo-N,N-2-trimethylpropenylamine after the reaction mixture has been concentrated.

$^1$H-NMR (300 MHz, CDCl$_3$): 6.64 (d, J=4, H-C(1)).

EXAMPLE 20

Methyl 2,3,4-tri-O-acetyl-1-deoxy-1-iodo-α-D-glucuronate is obtained quantitatively analogously to Example 1, starting from 227 mg (0.67 mmol) of methyl 2,3,4-tri-O-acetyl-D-glucuronate and 333 μl (2.03 mmol) of 1-iodo-N,N-2-trimethylpropenylamine after the reaction mixture has been concentrated.

$^1$H-NMR (300 MHz, CDCl$_3$): 7.02 (d, J=4.4, H-C(1)).

EXAMPLE 21

388 mg (90%) of heptaacetylcellobiosyl fluoride are obtained analogously to Example 1, starting from 433 mg (0.68 mmol) of heptaacetylcellobiose and 274 μl (1.36 mmol) of 1-fluoro-N,N-diisopropyl-2-methylpropenylamine.

$^1$H-NMR (300 MHz, CDCl$_3$): 5.36 (d, $J_{1,F}$=5.27, $J_{1,2}$=5.6; H-C-Cl).

What is claimed is:

1. A process for the preparation of a protected sugar halide or halogenated sugar derivative having an anomeric halogen atom by halogenating the anomeric hydroxy group, which comprises reacting one equivalent of a protected sugar or a protected sugar derivative, wherein said sugar derivative is a deoxy-sugar, amino-sugar, thio-sugar, sugar acid or an ester of a sugar acid having an anomeric hydroxyl group, with an equivalent of a secondary α-haloenamine in an inert solvent at a temperature between −20° and 80° C.

2. A process according to claim 1, wherein the solvent used is a halogenated aliphatic hydrocarbon, an aromatic hydrocarbon or an aliphatic ether.

3. A process according to claim 1, wherein the process is conducted in the presence of 1 to 3 equivalents of the α-haloenamine.

4. A process according to claim 1, which is carried out under an atmosphere of a protective gas.

5. A process according to claim 1, wherein the α-haloenamine has the formula I

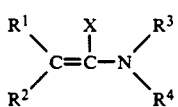

(I)

in which each of R$^1$ and R$^2$ independently of one another is linear or branched C$_1$-C$_{12}$alkyl, C$_4$-C$_7$cyclalkyl, C$_1$-C$_{12}$alkyl-C$_4$-C$_7$cycloalkyl, C$_4$-C$_7$cycloalkylmethyl, C$_1$-C$_{12}$alkyl-C$_4$-C$_7$cycloalkylmethyl, phenyl, C$_1$-C$_{12}$alkylphenyl, benzyl or C$_1$-C$_{12}$alkylbenzyl, or each of R$^1$ and R$^2$ together is tetramethylene, pentamethylene or hexamethylene; R$^3$ and R$^4$ independently of one another are linear or branched C$_1$-C$_{12}$alkyl, C$_4$-C$_7$cyclalkyl, C$_1$-C$_{12}$alkyl-C$_4$-C$_7$cycloalkyl, C$_4$-C$_7$cycloalkylmethyl, C$_1$-C$_{12}$alkyl-C$_4$-C$_7$cycloalkylmethyl, phenyl or benzyl, or R$^3$ and R$^4$ together are tetramethylene, pentamethylene or 3-oxa-1,5-pentylene; and X is halogen.

6. A process according to claim 5, wherein R$^1$ and R$^2$ independently of one another are C$_1$-C$_6$alkyl.

7. A process according to claim 6, wherein R$^1$ and R$^2$ are each methyl.

8. A process according to claim 5, wherein R$^3$ and R$^4$ independently of one another are C$_1$-C$_6$alkyl.

9. A process according to claim 8, wherein R$^3$ and R$^4$ are each C$_1$-C$_4$alkyl.

10. A process according to claim 8, wherein R$^3$ and R$^4$ are identical and are methyl, ethyl, n-propyl or isopropyl.

11. A process according to claim 1, wherein the protected sugar or sugar derivative is a monosaccharide or oligosaccharide or a monosaccharide or oligosaccharide derivative.

12. A process according to claim 11, wherein the protected monosaccharide or oligosaccharide is an aldose or ketose having an anomeric hydroxyl group.

13. A process according to claim 11, wherein the protected monosaccharide or oligosaccharide is an aldopyranose aldohexose, aldofuranose, ketopyranose or ketofuranose having an anomeric hydroxyl group.

14. A process according to claim 13, wherein the aldopyranose is D-ribose, D-arabinose, D-xylose, or D-lyxose; the aldohexose is D-allose, D-altrose, D-glucose, D-mannose, D-gulose, D-idose, D-galactose or D-talose; and the ketofuranose is D-psicose, D-fructose, D-sorbose or D-tagatose; the hydroxyl groups thereof, apart from the anomeric hydroxyl group, being protected.

15. A process according to claim 1, wherein the hydroxyl groups of the sugar or sugar derivative, apart from the anomeric hydroxyl group, are protected by C$_1$-C$_8$alkyl, trialkylsilyl having 3 to 20 C atoms, C$_7$-C$_{12}$aralkyl, C$_1$-C$_{12}$alkylidene, benzylidene, C$_2$-C$_{12}$acyl or R$^5$-SO$_2$-, R$^5$ being C$_1$-C$_{12}$alkyl, C$_5$cycloalkyl, C$_6$cycloalkyl, phenyl, benzyl, C$_1$-C$_{12}$alkylphenyl or C$_1$-C$_{12}$alkylbenzyl.

16. A process according to claim 1, wherein the reaction is begun at a temperature between −20° and 20° C. and allowed to proceed to complete conversion at an elevated temperature of up to 80° C.

17. A process according to claim 16, wherein the reaction is begun at a temperature of about 0° C. and allowed to proceed to complete conversion at an elevated temperature of up to 80° C.

* * * * *